United States Patent [19]

Davis

[11] Patent Number: 4,867,147

[45] Date of Patent: Sep. 19, 1989

[54] ORAL INJURY PREVENTION APPLIANCE FOR COMATOSE PATIENTS AND THE LIKE

[76] Inventor: E. Wayne Davis, 2035 Rivergate Dr., Knoxville, Tenn. 37920

[21] Appl. No.: 194,932

[22] Filed: May 17, 1988

[51] Int. Cl.$^4$ ............................................... A61F 5/56
[52] U.S. Cl. .................................... 128/859; 128/861
[58] Field of Search .................... 128/136, 860–861, 128/857, 862, 859; 433/5, 6, 7, 37, 38, 39, 140, 149

[56] References Cited

U.S. PATENT DOCUMENTS

| | | | |
|---|---|---|---|
| 1,302,004 | 4/1919 | Brown | 128/136 |
| 1,466,559 | 8/1923 | Purdy | 128/136 |
| 1,509,377 | 9/1924 | Rodgers | 433/37 |
| 2,694,397 | 11/1954 | Herns | 128/136 |
| 3,224,441 | 12/1965 | Monaghan | 128/136 |
| 3,307,539 | 3/1967 | Petersen | 128/136 |
| 4,055,895 | 11/1977 | Huge | 128/136 |
| 4,185,817 | 1/1980 | Peterson | 128/136 |

*Primary Examiner*—Robert A. Hafer
*Assistant Examiner*—Michael Brown
*Attorney, Agent, or Firm*—Pitts and Brittian

[57] ABSTRACT

An oral appliance to prevent further oral injury to comatose patients and the like. This appliance is a flat body of substantially uniform thickness that defines a U-shape. This provides an intra-oral leg for insertion between the occlusal surfaces of the teeth on one side of the patient's mouth. The second leg is extra-oral i.e., for exterior the mouth, with the curved surface between the legs fitting into the corner of the patient's mouth. This construction permits insertion in either side of the mouth, or periodic switching sides to prevent excessive irritation. A tether or lanyard is fastened to the extra-oral leg by providing a perforation near the distal end thereof. In the preferred embodiment, the extra-oral leg is both wider and longer than the intra-oral leg to facilitate manipulation by attending personnel. This appliance does not require impressions or the like, nor does it require extra-sedation of the patient for installation or manipulation. Further, it permits regular oral hygiene and regular oral inspection.

3 Claims, 2 Drawing Sheets

ORAL INJURY PREVENTION APPLIANCE FOR COMATOSE PATIENTS AND THE LIKE

TECHNICAL FIELD

This invention relates generally to appliances used to prevent oral injury, and more particularly to an oral appliance to prevent injury to the oral structures of critically comatose, heavily anesthetized or decerebrate patients.

BACKGROUND ART

The masticatory movements of the mandible of humans are normally rhythmic, automatic and powerful. Coordination of tongue movements with the masticating motion of the mandible is necessary and automatic in the normal chewing cycle. However, injury or alteration of the cerebral cortex, the reticular or pyramidal systems, the trigeminal nucleus or the hypothalamus can result in uncoordinated glossal movements in the comatose state of an individual. The comatose patient often exhibits powerful (300 psi) ruminatory reflex chewing patterns which are extremely difficult to control and frequently result in severe self-inflicted trauma to the soft tissues of the oral cavity, particularly the tongue. This often allows the tongue or cheek to become juxtapositioned between the teeth and this further aggravates the chewing reflex in the decerebrate state with extremely damaging results.

Several oral appliances have been used in attempts to prevent oral damage by the patient. These include intermaxillary fixation using arch wires in combination with hard acrylic devices. Also, hard rubber or plastic mouth props, plastic airways and flexible or inflexible bite splints over the occlusal surfaces of the teeth have been used. Typical of the appliances of the prior art are described in U.S. Pat. Nos. 1,466,559, issued to C. G. Purdy on Aug. 28, 1923; 2,694,397, issued to F. W. Herms on Nov. 16, 1954; 3,307,539, issued to G. A. Peterson on Mar. 7, 1967; and 4,041,937, issued to M. Diaz on Aug. 16, 1977. Other work in this field appears in the following publications: "A Tongue Stent for Prevention of Oral Trauma in the Comatose Patient", G. E. Hanson, et al., Critical Care Medicine, Vol. 3, No. 5, p. 200 (1975); "The Use of Tongue-Depressing Stents for Neuropathologic Chewing", M. J. Jackson, Jl. Prosthetic Dentistry, Vol. 40, No. 3, p. 309 (1978); "An Occlusal Prosthesis to Assure Airway Patency in the Comatose Patient", W. A. Levine, et al., Jl. Prosthetic Dentistry, Vol. 44, No. 4, p. 451 (1980); and "Prevention of Self-Inflicted Trauma in Comatose Patients", T. E. D. Peters, et al., Oral Surgery, Vol. 57, No. 4, p. 367 (1980).

Many of the prior art appliances have been found to actually worsen an already severe problem. If the wire or rigid plastic components break they create jagged, virtually non-detectable foreign bodies which may be aspirated into the lungs. These may also lacerate the throat, larynx or soft tissue of the oral cavity. The non-flexible nature of these appliances often cause fractures of the occlusal and incisal surfaces of the teeth, especially if the teeth have been restored with amalgam or composite material. The fractured filling material and tooth fragments also become foreign bodies. Exposure of vital pulp tissue is common in tooth fracture situations creating even further complications.

Many of the prior devices require the use of impressions or molds to obtain positional relationships of the teeth. For patients of the type having involuntary mandible motions, these impressions must be made while the patient is under heavy sedation or general anesthesia. Some appliances can only be inserted under such sedated conditions. The sedation of a comatose patient is always dangerous. Further, materials used in making the impression introduce problems similar to those generated by breakage of the appliance itself during use.

The comatose state of a patient can be relatively short, as after surgery under a general anesthesia, or very extended due to an accident, stroke or the like. For extended comatose times, frequent oral hygiene steps and periodic oral examination are desirable; however, the appliances of the prior art generally prevent such actions. Often the care of long-term comatose patients is the responsibility of a family member. As such, the family member is unable to cope with problems generated by the appliances of the prior art. Furthermore, just as turning of a patient in bed to prevent bedsores and stiffness is desirable, a periodic change of appliance position is desirable to prevent chronic soreness and cutting of the mouth. This is not possible with the prosthesis units known in the art.

Accordingly, it is an object of the present invention to provide a simple oral appliance to prevent damage to the teeth or surrounding soft tissue of a comatose patient or the like.

It is another object to provide an oral injury prevention device that is resilient and flexible, with properties to withstand extreme and prolonged biting force without becoming fragmented or perforated.

An additional object is to provide an oral appliance for use with a comatose patient that does not interfere with normal mandibular movements, such as yawning and lateral movements, and permits regular oral hygiene and oral examination.

A further object is to provide an oral appliance that does not require the making of impressions or the use of any special sedation for installation, removal, or maintenance.

It is also an object of the present invention to provide an oral appliance for use with comatose patients and the like that can be easily switched from side-to-side by either medically skilled or unskilled attendants of the patient.

These and other objects of the present invention will become apparent upon a consideration of the drawings of the invention when reviewed in light of the detailed description that follows.

DISCLOSURE OF THE INVENTION

In accordance with the above-cited objects, the present invention is a flat, relatively thin appliance formed generally in a U-shape, one leg thereof forming an extra-oral portion, and the other leg an intra-oral portion for placement between the occlusal surfaces of the upper and lower teeth to prevent full closure. This intra-oral portion is slightly wider than the surface of the posterior teeth so as to maintain the tongue and cheek away from the teeth. The central portion of the U receives the lip at the corner of the mouth to prevent excessive movement into the mouth, and the extra-oral portion extends against the cheek surface. Means are provided to fasten this extra-oral portion to the patient to prevent dislodgement or loss thereof. This can take the form of a cord threaded through a hole in the distal end of the appliance. In the preferred embodiment, the extra-oral portion is both wider and longer than the intra-oral portion to make manipulation and positioning of the appliance by attending personnel easier. This also significantly lessens the real probability of the attendee being severely bitten by the patient.

BEST MODE FOR CARRYING OUT THE INVENTION

Figure 1:
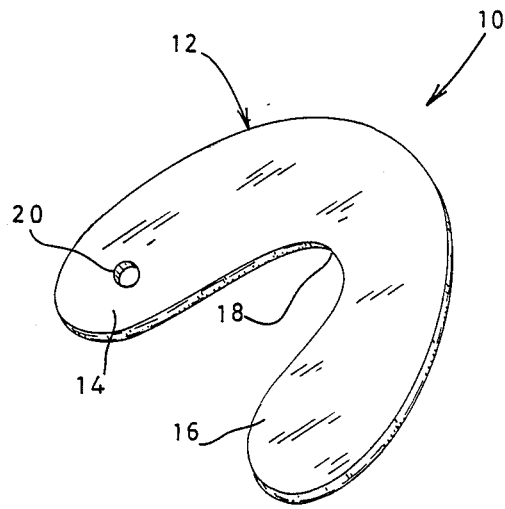
FIG. 1 is a perspective drawing of the oral appliance of the present invention.
Figure 2:
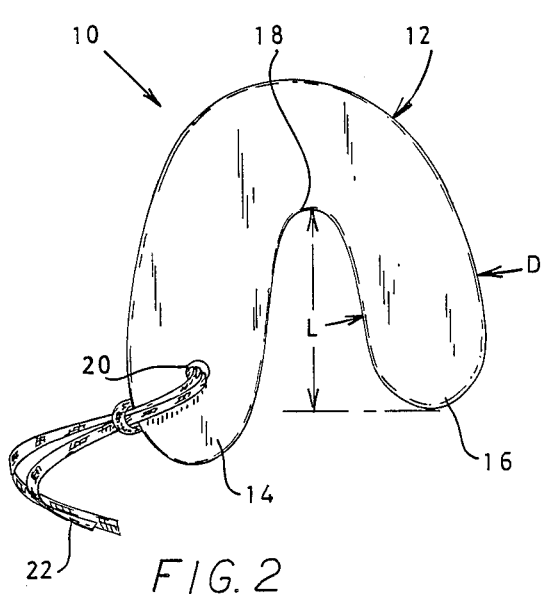
FIG. 2 is a plan view of the appliance of FIG. 1.
Figure 3:
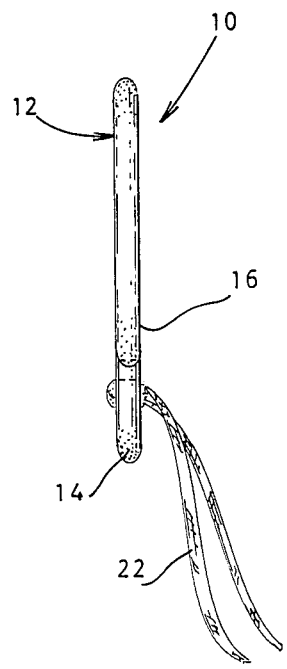
FIG. 3 is an edge view of the appliance as seen from the right hand side of FIG. 2.

The present invention is illustrated generally at 10 in FIGS. 1 through 3. This oral appliance is formed from a flat sheet of polyvinyl chloride or similar flexible and durable material. Typically, this is about 3 mm in thickness, although other thicknesses can be used. For example, if a patient already has inflicted severe damage, up to 6 mm thickness can be utilized. Preferably, the sheet material has a color (e.g., blue) to be acceptable in medical facilities and yet permit the appliance to be seen so as to permit surveillance of its position in the mouth of a patient. A suitable material for fabricating the present invention is "Sta-Guard" mouthguard material distributed by the Stalite Division of Buffalo Dental Manufacturing Co., Inc., Syosset, N.Y.

The appliance 10 has a generally U-shaped body 12 formed by an extra-oral leg 14 and an intra-oral leg 16. These define a centrally curved contour 18 therebetween. The intra-oral portion 16 has a length, L, from this curve 18 to its distal end sufficient to reach rearward teeth; and has a width, D, slightly in excess (e.g., 4–6 mm) of the width of the patient's teeth. The dimensions for a given patient will depend upon the size of the oral cavity and can be adjusted using ordinary cutting instruments. The extra width excludes both the tongue and the cheek from a position between the teeth so as to prevent injury to this soft tissue of the oral cavity. The edges of the body 12 are rounded to prevent irritation.

Figure 5:
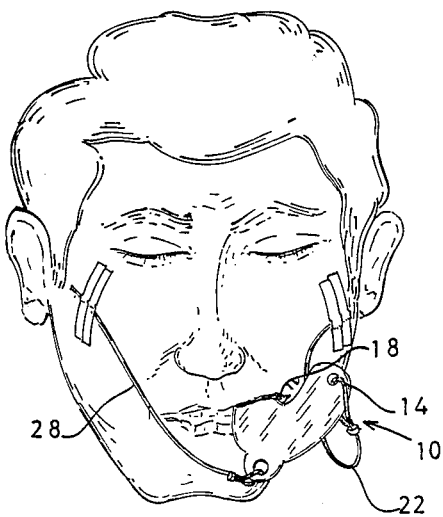
FIG. 5 is a drawing illustrating how the present invention fits into a user's mouth

The extra-oral portion 14 of the body 12 is provided with a perforation 20 proximate its distal end. Threaded through this perforation is a soft cord (nylon umbilical cord or trachaeostomy tape, for example) or other tether 22 which can be attached to the cheek of a patient as with tape or the like. This is depicted in FIG. 5 This helps maintain the appliance in place, and prevents loss if the appliance is dislodged from the mouth.

In the preferred embodiment, the extra-oral portion is made both wider and longer than the intra-oral portion. This increases the overall width of the appliance to prevent swallowing or aspiration, and also makes the manipulation and positioning of the appliance easier by attending personnel.

Figure 4:
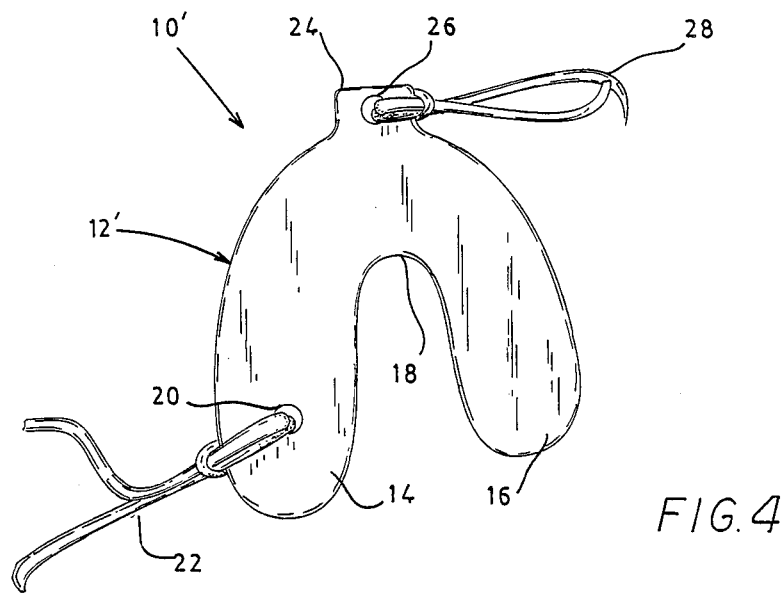
FIG. 4 is a plan view of another embodiment of the present invention.

Another embodiment of the present invention is illustrated at 10' in FIG. 4. The body 12' is modified so as to provide a tab 24 proximate the junction of the intra- and extra-oral portions 16, 14, respectively, and generally opposite the curved contour 18. This tab can be provided with an aperture 26 for receiving second tether element 28; thus, permitting fastening to an opposite cheek of a patient if desired or necessary. Further, the tab provides extra surface for grasping of the appliance during insertion or removal of the intra-oral portion relative to a patient.

Due to the construction of the appliance of the present invention, insertion or removal can be accomplished without any special sedation of the patient. In fact, it can be inserted by paramedics at the scene of an accident, etc., where comatose persons are involved. Its simplicity permits regular oral hygiene, and it can be switched from one side of the mouth to the other to prevent excessive irritation to the mouth corner. This also prevents unilateral compression to the teeth and their supporting structures. Furthermore, due to the durability and flexibility, there can be no fragmenting to create problems, and the texture prevents further damage while allowing the healing of traumatized tissues.

Although the appliance of the present invention has been discussed for use with comatose patients, it is equally suitable for use with decerebrate (without brain function), heavily anesthetized or grand mal epileptic patients. While the invention has been described with certain specificities for purposes of clarity and understanding, it is to be understood that certain changes and modifications come within the scope of the appended claims and their equivalents, when read together with the detailed description of the invention.

I claim:

1. An oral injury prevention appliance for insertion in the mouth for use with comatose patients and the like, which comprises a U-shaped resilient body member of substantially uniform thickness and rounded edges, which body member defines:

a first leg as an intra-oral portion for placement between the occlusal surfaces on one side of said patient's mouth, said intra-oral portion having a length sufficient to extend proximate a rear of said occlusal surfaces, and a width in excess of the width of said occlusal surfaces to exclude soft tissue from said occlusal surfaces;

a second leg as an extra-oral portion to contact the exterior of said patient's cheek spaced from said first leg a distance to accommodate the thickness of said cheek, said extra-oral portion provided with a perforation proximate a distal end thereof to receive a surgical tether for use to attach said appliance to said patient, said extra-oral portion having a length and a width greater than the length and width of said intra-oral portion; and a cured junction portion connected between said first leg and said second leg to rest against a corner of said patient's mouth to limit movement of said first leg into said patient's mouth.

2. The appliance of claim 1 further comprising a tab member extending from said body member proximate said junction portion between said first leg and said second leg, said body member being provided with a second perforation through a central portion of said tab member, and further comprises a second tether member passing through said second perforation to attach said appliance to said patient.

3. An oral appliance for insertion in the mouth for use with comatose patients and the like to prevent self-inflicted trauma to the soft tissue of the oral cavity of the patient, which comprises a U-shaped resilient body member of substantially uniform thickness and rounded edges, which body member defines:

a first leg as an intra-oral portion for placement between occlusal surfaces on one side of said patient's mouth, said intra-oral portion having a length sufficient to extend proximate a rear of said occlusal surfaces and a width in excess of the width of said occlusal surfaces to exclude soft tissue from said occlusal surfaces;

a second leg as an extra-oral portion spaced from said intra-oral portion a substantially uniform distance to accommodate the thickness of a cheek of said patient, said extra-oral portion having a length and a width greater than the length and width of said intra-oral portion so as to contact the exterior of said cheek of said patient to prevent rotation of said appliance in said patient's mouth and provide for grasp of said appliance during insertion and removal from said patient's mouth, said extra-oral portion being provided with a perforation proximate a distal end thereof to receive a surgical tether for use to attach said appliance to said patent; and a curved junction portion connected between said first leg and said second leg to rest against a corner of said patient's mouth to limit movement of said first leg into said patient's mouth.

* * * * *